(12) United States Patent
Enari et al.

(10) Patent No.: US 8,283,311 B2
(45) Date of Patent: Oct. 9, 2012

(54) PEPTIDE-CONTAINING FOOD INTAKE REGULATOR

(75) Inventors: Hiroyuki Enari, Tsukuba (JP);
Motohiko Tada, Tsukuba (JP);
Yoshinori Takahashi, Tsukuba (JP);
Masataka Kawarasaki, Tsukuba (JP)

(73) Assignee: Maruha Nichiro Foods, Inc. (JP)

( * ) Notice: Subject to any disclaimer, the term of this patent is extended or adjusted under 35 U.S.C. 154(b) by 570 days.

(21) Appl. No.: 12/397,034

(22) Filed: Mar. 3, 2009

(65) Prior Publication Data

US 2009/0275500 A1 Nov. 5, 2009

(30) Foreign Application Priority Data

Mar. 4, 2008 (JP) ................................ 2008-054126

(51) Int. Cl.
*A61K 38/10* (2006.01)
*C07K 7/08* (2006.01)
(52) U.S. Cl. .......... 514/4.9; 514/5.3; 514/21.5; 530/327
(58) Field of Classification Search .................. None
See application file for complete search history.

(56) References Cited

U.S. PATENT DOCUMENTS

| | | | | |
|---|---|---|---|---|
| 5,849,708 | A * | 12/1998 | Maratos-Flier | 514/4.8 |
| 2003/0224988 | A1 | 12/2003 | Maratos-Flier et al. | |
| 2004/0086941 | A1* | 5/2004 | Mori et al. | 435/7.1 |
| 2005/0191241 | A1 | 9/2005 | Zagon et al. | |
| 2006/0040872 | A1* | 2/2006 | Osajima et al. | 514/19 |

FOREIGN PATENT DOCUMENTS

| | | |
|---|---|---|
| JP | 63-129949 A | 6/1988 |
| JP | 09-020675 A | 1/1997 |
| JP | 11-507517 A | 7/1999 |
| JP | 2002-053474 A | 2/2002 |
| WO | 96/39162 A1 | 12/1996 |
| WO | 97/36608 A1 | 10/1997 |
| WO | 9802165 A1 | 1/1998 |
| WO | 01/70031 A1 | 9/2001 |
| WO | 02/092018 A2 | 11/2002 |
| WO | 2009/033701 A1 | 3/2009 |
| WO | 2009/033707 A2 | 3/2009 |
| WO | 2009/033717 A2 | 3/2009 |
| WO | 2009/033724 A1 | 3/2009 |
| WO | 2009/033735 A2 | 3/2009 |
| WO | 2009/033744 A1 | 3/2009 |
| WO | 2009/033795 A2 | 3/2009 |
| WO | 2009/039990 A2 | 4/2009 |
| WO | 2009/040020 A1 | 4/2009 |
| WO | 2009/043439 A2 | 4/2009 |

(Continued)

OTHER PUBLICATIONS

Bednarek et al. Short Segment of Human Melanin-Concentrating Hormone . . . Biochemistry. 2001, vol. 40, No. 31, pp. 9379-9386.*

(Continued)

*Primary Examiner* — Jeffrey E Russel
(74) *Attorney, Agent, or Firm* — Cantor Colburn LLP

(57) ABSTRACT

A safe and widely-applicable food intake regulator can be provided by using at least one peptide selected from the group consisting of a fish or mammalian melanin-concentrating hormone (MCH) and enzymatic digests thereof, which have the activity to suppress food intake.

7 Claims, 1 Drawing Sheet

FOREIGN PATENT DOCUMENTS

| WO | 2009/043448 A2 | 4/2009 |
| --- | --- | --- |
| WO | 2009/043450 A2 | 4/2009 |
| WO | 2009/043457 A2 | 4/2009 |
| WO | 2009/043458 A2 | 4/2009 |
| WO | 2009/043466 A2 | 4/2009 |
| WO | 2009/043505 A2 | 4/2009 |
| WO | 2009/043527 A2 | 4/2009 |
| WO | 2009/046844 A1 | 4/2009 |
| WO | 2009/046852 A1 | 4/2009 |
| WO | 2009/046861 A1 | 4/2009 |
| WO | 2009/046865 A2 | 4/2009 |

OTHER PUBLICATIONS

Kawazoe et al. Structure-activity relationships of melanin-concentrating hormone. International Journal of Peptide and Protein Research. 1987, vol. 29, pp. 714-721.*

European Search Report for European Application No. 09154306.6-2107 dated Jul. 16, 2009.

Rejection Notice for Japanese Application No. 2008-054126 with English translation dated Jun. 2, 2010.

Matsuda K et al: "Central administration of melanin-concentrating hormone (MCH) suppresses food intake, but not locomotor activity, in the goldfish, Carassius auratus" Neuroscience Letters, Limerick IE, vol. 399, No. 3, May 22, 2006, pp. 259-263, XP025024251 ISSN: 0304-3940 [retrieved on May 22, 2006] p. 261.

Rossi M et al: "Melanin-concentrating hormone acutely stimulates feeding, but chronic administration has no effect on body weight" Endocrinology, vol. 138, No. 1, 1997, pp. 351-355, ISSN: 0013-7227.

Presse F et al: "Melanin-concentrating hormone is a potent anorectic peptide regulated by food-deprivation and glucopenia in the rat" Neuroscience, vol. 71, No. 3, 1996, pp. 735-745, XP002535523 ISSN: 0306-4522.

Database Biosis [online] Biosciences Information Service, Philadelphia PA, US; 1996, Rovere Carole et al: "Impaired processinf of brain proneurotensin and promelanin-concentrating hormone in obese fat/fat mice" XP002535524 Database accession No. PREV199699091708.

Shimada et al., Mice lacking melanin-concentrating hormone are hypophagic and lean, Nature, Dec. 17, 1998;396:670-4.

Takekawa et al., T-226296: a novel, orally active and selective melanin-concentrating hormone receptor antagonist, Eur J Pharmacol, 2002, 438: 129-35.

Rossi et al., Melanin-concentrating hormone acutely stimulates feeding, but chronic administration has no effect on body weight, Endocrinology. Jan. 1997;138(1):351-5.

* cited by examiner

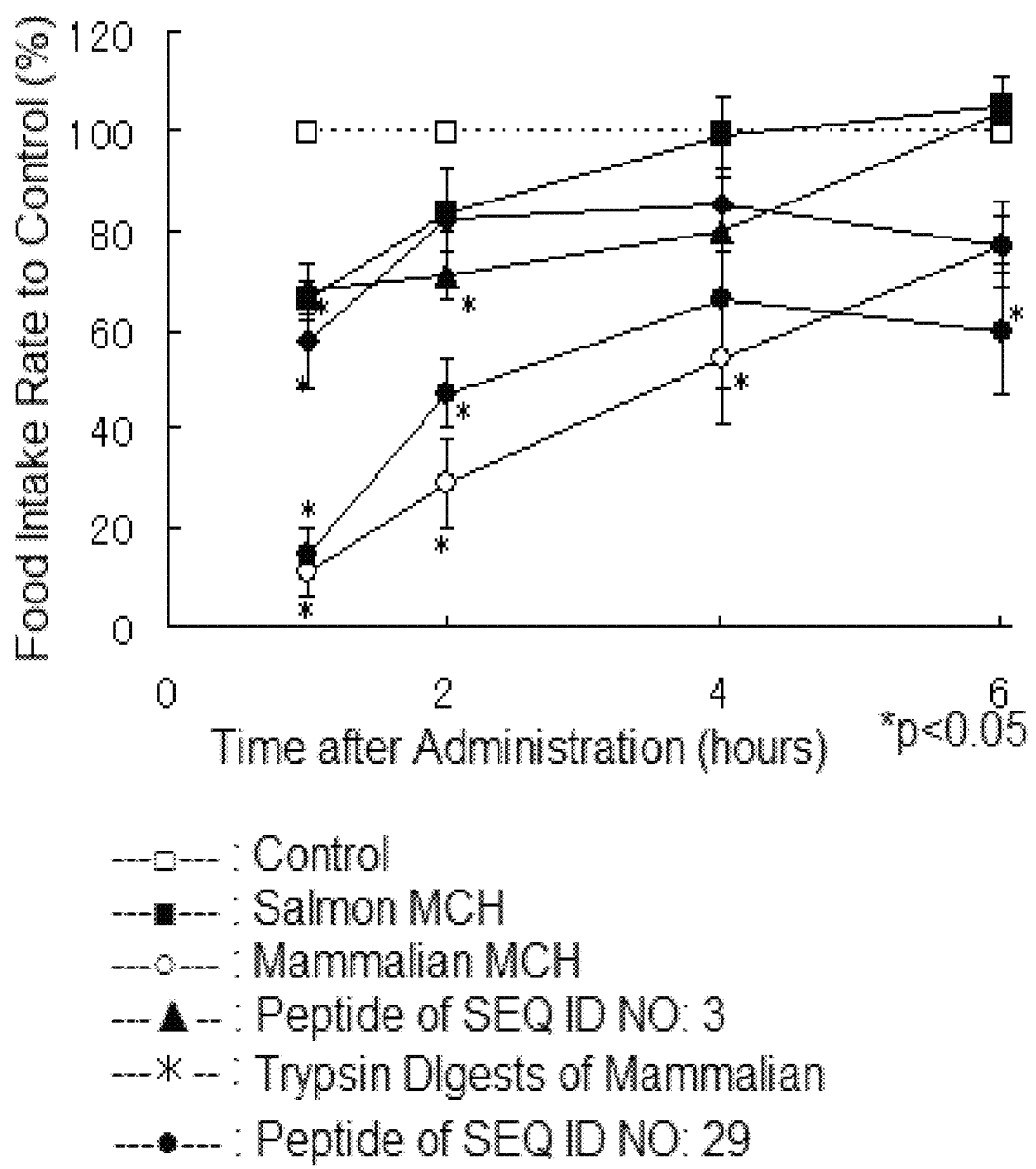

SEQUENCE LISTING

```
<160> NUMBER OF SEQ ID NOS: 34

<210> SEQ ID NO 1
<211> LENGTH: 17
<212> TYPE: PRT
<213> ORGANISM: Oncorhynchus keta
<220> FEATURE:
<221> NAME/KEY: DISULFID
<222> LOCATION: (5)..(14)
```

```
<400> SEQUENCE: 1

Asp Thr Met Arg Cys Met Val Gly Arg Val Tyr Arg Pro Cys Trp Gln
1               5                   10                  15

Val

<210> SEQ ID NO 2
<211> LENGTH: 19
<212> TYPE: PRT
<213> ORGANISM: Homo sapiens
<220> FEATURE:
<221> NAME/KEY: DISULFID
<222> LOCATION: (7)..(16)

<400> SEQUENCE: 2

Asp Phe Asp Met Leu Arg Cys Met Leu Gly Arg Val Tyr Arg Pro Cys
1               5                   10                  15

Trp Gln Val

<210> SEQ ID NO 3
<211> LENGTH: 19
<212> TYPE: PRT
<213> ORGANISM: Homo sapiens

<400> SEQUENCE: 3

Asp Phe Asp Met Leu Arg Cys Met Leu Gly Arg Val Tyr Arg Pro Cys
1               5                   10                  15

Trp Gln Val

<210> SEQ ID NO 4
<211> LENGTH: 6
<212> TYPE: PRT
<213> ORGANISM: Homo sapiens

<400> SEQUENCE: 4

Asp Phe Asp Met Leu Arg
1               5

<210> SEQ ID NO 5
<211> LENGTH: 5
<212> TYPE: PRT
<213> ORGANISM: Homo sapiens

<400> SEQUENCE: 5

Asp Phe Asp Met Leu
1               5

<210> SEQ ID NO 6
<211> LENGTH: 4
<212> TYPE: PRT
<213> ORGANISM: Homo sapiens

<400> SEQUENCE: 6

Asp Met Leu Arg
1

<210> SEQ ID NO 7
<211> LENGTH: 4
<212> TYPE: PRT
<213> ORGANISM: Homo sapiens

<400> SEQUENCE: 7

Arg Cys Met Leu
1
```

```
<210> SEQ ID NO 8
<211> LENGTH: 4
<212> TYPE: PRT
<213> ORGANISM: Homo sapiens
<220> FEATURE:
<221> NAME/KEY: DISULFID
<222> LOCATION: (2)..(2)
<223> OTHER INFORMATION: To C3 of SEQ ID NO:30 or to C3 of SEQ ID NO:24

<400> SEQUENCE: 8

Arg Cys Met Leu
1

<210> SEQ ID NO 9
<211> LENGTH: 6
<212> TYPE: PRT
<213> ORGANISM: Homo sapiens
<220> FEATURE:
<221> NAME/KEY: DISULFID
<222> LOCATION: (3)..(3)

<400> SEQUENCE: 9

Arg Pro Cys Trp Gln Val
1               5

<210> SEQ ID NO 10
<211> LENGTH: 3
<212> TYPE: PRT
<213> ORGANISM: Homo sapiens

<400> SEQUENCE: 10

Met Leu Gly
1

<210> SEQ ID NO 11
<211> LENGTH: 3
<212> TYPE: PRT
<213> ORGANISM: Homo sapiens

<400> SEQUENCE: 11

Leu Gly Arg
1

<210> SEQ ID NO 12
<211> LENGTH: 4
<212> TYPE: PRT
<213> ORGANISM: Homo sapiens

<400> SEQUENCE: 12

Gly Arg Val Tyr
1

<210> SEQ ID NO 13
<211> LENGTH: 5
<212> TYPE: PRT
<213> ORGANISM: Homo sapiens

<400> SEQUENCE: 13

Leu Gly Arg Val Tyr
1               5

<210> SEQ ID NO 14
<211> LENGTH: 2
<212> TYPE: PRT
<213> ORGANISM: Homo sapiens
```

```
<400> SEQUENCE: 14

Val Tyr
1

<210> SEQ ID NO 15
<211> LENGTH: 6
<212> TYPE: PRT
<213> ORGANISM: Homo sapiens
<220> FEATURE:
<221> NAME/KEY: DISULFID
<222> LOCATION: (4)..(4)

<400> SEQUENCE: 15

Met Leu Arg Cys Met Leu
1               5

<210> SEQ ID NO 16
<211> LENGTH: 6
<212> TYPE: PRT
<213> ORGANISM: Homo sapiens
<220> FEATURE:
<221> NAME/KEY: DISULFID
<222> LOCATION: (3)..(3)

<400> SEQUENCE: 16

Arg Pro Cys Trp Gln Val
1               5

<210> SEQ ID NO 17
<211> LENGTH: 5
<212> TYPE: PRT
<213> ORGANISM: Homo sapiens
<220> FEATURE:
<221> NAME/KEY: DISULFID
<222> LOCATION: (3)..(3)

<400> SEQUENCE: 17

Arg Pro Cys Trp Gln
1               5

<210> SEQ ID NO 18
<211> LENGTH: 6
<212> TYPE: PRT
<213> ORGANISM: Homo sapiens
<220> FEATURE:
<221> NAME/KEY: DISULFID
<222> LOCATION: (3)..(3)

<400> SEQUENCE: 18

Arg Pro Cys Trp Gln Val
1               5

<210> SEQ ID NO 19
<211> LENGTH: 6
<212> TYPE: PRT
<213> ORGANISM: Homo sapiens
<220> FEATURE:
<221> NAME/KEY: DISULFID
<222> LOCATION: (3)..(3)
<223> OTHER INFORMATION: To C1 of SEQ ID NO:31

<400> SEQUENCE: 19

Arg Pro Cys Trp Gln Val
1               5
```

```
<210> SEQ ID NO 20
<211> LENGTH: 5
<212> TYPE: PRT
<213> ORGANISM: Homo sapiens
<220> FEATURE:
<221> NAME/KEY: DISULFID
<222> LOCATION: (2)..(2)
<223> OTHER INFORMATION: To C1 of SEQ ID NO:32

<400> SEQUENCE: 20

Pro Cys Trp Gln Val
1               5

<210> SEQ ID NO 21
<211> LENGTH: 8
<212> TYPE: PRT
<213> ORGANISM: Homo sapiens
<220> FEATURE:
<221> NAME/KEY: DISULFID
<222> LOCATION: (5)..(5)
<223> OTHER INFORMATION: To  C1 of SEQ ID NO:31

<400> SEQUENCE: 21

Val Tyr Arg Pro Cys Trp Gln Val
1               5

<210> SEQ ID NO 22
<211> LENGTH: 6
<212> TYPE: PRT
<213> ORGANISM: Homo sapiens
<220> FEATURE:
<221> NAME/KEY: DISULFID
<222> LOCATION: (3)..(3)

<400> SEQUENCE: 22

Arg Pro Cys Trp Gln Val
1               5

<210> SEQ ID NO 23
<211> LENGTH: 8
<212> TYPE: PRT
<213> ORGANISM: Homo sapiens
<220> FEATURE:
<221> NAME/KEY: DISULFID
<222> LOCATION: (5)..(5)

<400> SEQUENCE: 23

Val Tyr Arg Pro Cys Trp Gln Val
1               5

<210> SEQ ID NO 24
<211> LENGTH: 6
<212> TYPE: PRT
<213> ORGANISM: Homo sapiens
<220> FEATURE:
<221> NAME/KEY: DISULFID
<222> LOCATION: (3)..(3)
<223> OTHER INFORMATION: To C2 of SEQ ID NO:8

<400> SEQUENCE: 24

Arg Pro Cys Trp Gln Val
1               5

<210> SEQ ID NO 25
<211> LENGTH: 8
<212> TYPE: PRT
<213> ORGANISM: Homo sapiens
```

```
<220> FEATURE:
<221> NAME/KEY: DISULFID
<222> LOCATION: (5)..(5)
<223> OTHER INFORMATION: To C2 of SEQ ID NO:33

<400> SEQUENCE: 25

Val Tyr Arg Pro Cys Trp Gln Val
1               5

<210> SEQ ID NO 26
<211> LENGTH: 8
<212> TYPE: PRT
<213> ORGANISM: Homo sapiens

<400> SEQUENCE: 26

Val Tyr Arg Pro Cys Trp Gln Val
1               5

<210> SEQ ID NO 27
<211> LENGTH: 6
<212> TYPE: PRT
<213> ORGANISM: Homo sapiens

<400> SEQUENCE: 27

Arg Pro Cys Trp Gln Val
1               5

<210> SEQ ID NO 28
<211> LENGTH: 4
<212> TYPE: PRT
<213> ORGANISM: Homo sapiens

<400> SEQUENCE: 28

Cys Trp Gln Val
1

<210> SEQ ID NO 29
<211> LENGTH: 14
<212> TYPE: PRT
<213> ORGANISM: Homo sapiens

<400> SEQUENCE: 29

Arg Cys Met Leu Gly Arg Val Tyr Arg Pro Cys Trp Gln Val
1               5                   10

<210> SEQ ID NO 30
<211> LENGTH: 4
<212> TYPE: PRT
<213> ORGANISM: Homo sapiens
<220> FEATURE:
<221> NAME/KEY: DISULFID
<222> LOCATION: (3)..(3)
<223> OTHER INFORMATION: To C of SEQ ID NO:8

<400> SEQUENCE: 30

Arg Pro Cys Trp
1

<210> SEQ ID NO 31
<211> LENGTH: 5
<212> TYPE: PRT
<213> ORGANISM: Homo sapiens
<220> FEATURE:
<221> NAME/KEY: DISULFID
<222> LOCATION: (1)..(1)
<223> OTHER INFORMATION: To C3 in SEQ ID NO:19 or to C5 in SEQ ID NO:21
```

```
<400> SEQUENCE: 31

Cys Met Leu Gly Arg
1               5

<210> SEQ ID NO 32
<211> LENGTH: 6
<212> TYPE: PRT
<213> ORGANISM: Homo sapiens
<220> FEATURE:
<221> NAME/KEY: DISULFID
<222> LOCATION: (1)..(1)
<223> OTHER INFORMATION: To C2 of SEQ ID NO:20

<400> SEQUENCE: 32

Cys Met Leu Gly Arg Val
1               5

<210> SEQ ID NO 33
<211> LENGTH: 5
<212> TYPE: PRT
<213> ORGANISM: Homo sapiens
<220> FEATURE:
<221> NAME/KEY: DISULFID
<222> LOCATION: (2)..(2)
<223> OTHER INFORMATION: To C5 of SEQ ID NO:25

<400> SEQUENCE: 33

Arg Cys Met Leu Gly
1               5

<210> SEQ ID NO 34
<211> LENGTH: 10
<212> TYPE: PRT
<213> ORGANISM: Homo sapiens

<400> SEQUENCE: 34

Gly Arg Val Tyr Arg Pro Cys Trp Gln Val
1               5                   10
```

PEPTIDE-CONTAINING FOOD INTAKE REGULATOR

CROSS REFERENCE TO RELATED APPLICATION

This application claims priority to Japanese Application No. 2008-054126, filed Mar. 4, 2008, which is hereby incorporated by reference in its entirety.

BACKGROUND OF THE INVENTION

1. Field of the Invention

The present invention relates to a food intake regulator, which contains a fish or mammalian melanin-concentrating hormone (MCH) and related substances thereof as an active ingredient. The food intake regulator according to the invention is useful in treatment of a disease and improvement of the symptom of the disease that are due to overeating or that require feeding regulation. Therefore, the food intake regulator according to the invention can be widely applied to various foods and pharmaceuticals.

2. Description of the Related Art

About more than half of men and women in their 40s or higher are patients or potential patients of lifestyle-related diseases such as hypertension, diabetes mellitus, and hyperlipidemia. Since most of these diseases are due to obesity, it is desired that obesity be prevented or improved. The best approach to preventing obesity is considered to setting of a regular eating pattern, but it is often difficult to establish and maintain the pattern in the modern age as a time of plenty.

As a substance which regulates, especially suppresses food intake, mazindol as amphetamines is commercially available as a pharmaceutical. However, the use of mazindol is limited only to patients having severe obesity because of the direct effects of mazindol on the central nervous system and risks of habituation or addiction. Safer approaches for the food intake regulation have been required.

As a method of suppressing food intake, Japanese Patent Laid-Open No. 2000-515139 discloses one using precursors of serotonin, dopamine, norepinephrine and histamine; Japanese Patent Laid-Open No. 1997-20675 discloses one using a fruit body of pleurotus ostreatus; and Japanese Patent Laid-Open No. 2002-53474 discloses one using avocado.

It is known that various hormones involved in food intake are present in the brain. As food intake stimulators, there are melanin-concentrating hormone (MCH), neuropeptide Y, peptide YY, AgRP, ghrelin, and noradrenaline, while, as biologically active substances for food intake regulators, there are α-melanocyte-stimulating hormone (α-MSH), serotonin, cholecystokinin (CCK), and glucagon-like peptide-1 (GLP-1).

Melanin-concentrating hormone (MCH), which was first identified as a substance adaptively controlling pigment aggregation in the pituitary gland of salmon of fishes, was also found in the hypothalamus of the mammalian brain and attracts attention as a hormone involved in food intake. Significant body weight loss was found in MCH gene knockout mice with decreased food intake and increased metabolism (Shimada. M, et al., Nature, 396, 670-674, 1998). In addition, after MCH was injected intracerebroventricularly to rats, it was found to stimulate food intake (M. Rossi, et. al., Endocrinology, 138, 351-355, 1997).

Thus, an antagonist of the receptor for MCH as a food intake stimulator is expected to provide a food intake regulator. For this reason, many MCH receptor antagonists have been developed and expected to provide an anti-obesity agent, such as the food intake regulator i T-226296 (Takekawa, S., et. al., European Journal of Pharmacology, 438(3), 129-135, 2002).

SUMMARY OF THE INVENTION

As mentioned above, melanin-concentrating hormone (MCH) is known as a substance involved in food intake, especially a substance having the ability to stimulate food intake, but there is no reports looking at another aspect of MCH as a food intake regulator.

In light of the related art, an object of the present invention is to provide a food intake regulator which can be administered for medical treatment by a suitable manner such as intravenous injection and easily be taken as a food.

The present inventors have conducted extensive studies to achieve the above object and found that melanin-concentrating hormone (MCH) and enzymatic digests thereof unexpectedly have the ability to regulate food intake and that they are safe and useful. These findings have led the inventors to complete the invention. The findings of the inventors are novel and not known in the prior art.

Therefore, the first object of the present invention is to provide a peptide or a peptide composition which exhibits food intake regulation activity. The first object of the present invention is to provide further foods, pharmaceuticals, quasi drugs, and cosmetics containing the peptide or the peptide composition.

The second object of the invention is to provide a process for producing a peptide and enzymatic digest peptides thereof useful for the active ingredient as the food intake regulator.

The present invention includes the following embodiments:

The food intake regulator according to the present invention comprises, as an active ingredient, at least one component selected from the group consisting of:

(A) a fish melanin-concentrating hormone which is a peptide represented by the following formula (1) (SEQ ID NO: 1):

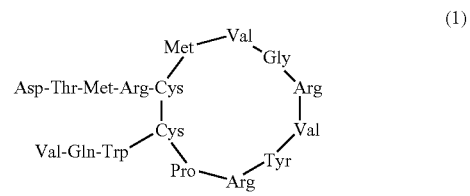

and salts thereof;

(B) a mammalian melanin-concentrating hormone which is a peptide represented by the following formula (2) (SEQ ID NO: 2):

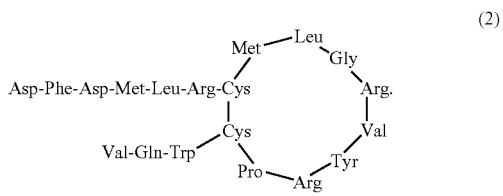

and salts thereof;

(C) a peptide consisting of an amino acid sequence represented by Asp Phe Asp Met Leu Arg Cys Met Leu Gly Arg Val Tyr Arg Pro Cys Trp Gln Val (SEQ ID NO: 3) and salts thereof;

(D) a peptide represented by one of the following amino acid sequence represented by any one of the following (i) to (xxv) and salts thereof:

(i) Asp Phe Asp Met Leu Arg (SEQ ID NO: 4)

(ii) Asp Phe Asp Met Leu (SEQ ID NO: 5)

(iii) Asp Met Leu Arg (SEQ ID NO: 6)

(iv) Arg Cys Met Leu (SEQ ID NO: 7)

(v) Disulfide bond between Arg Cys Met Leu (SEQ ID NO: 8) and Arg Pro Cys Trp (SEQ ID NO: 30):

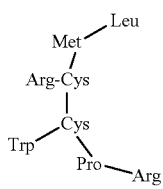

(vi)

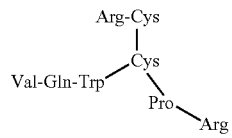 (SEQ ID NO: 9)

(vii) Met Leu Gly (SEQ ID NO: 10)

(viii) Leu Gly Arg (SEQ ID NO: 11)

(ix) Gly Arg Val Tyr (SEQ ID NO: 12)

(x) Leu Gly Arg Val Tyr (SEQ ID NO: 13)

(xi) Val Tyr (SEQ ID NO: 14)

(xii)

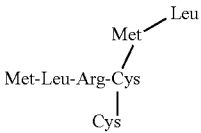 (SEQ ID NO: 15)

(xiii)

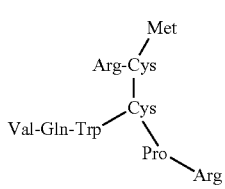 (SEQ ID NO: 16)

(xiv)

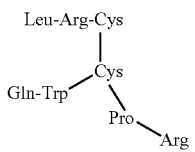 (SEQ ID NO: 17)

(xv)

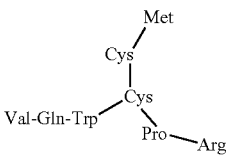 (SEQ ID NO: 18)

(xvi) Disulfide bond between CysMetLeuGlyArg (SEQ ID NO: 31) and ArgProCysTrpGlnVal (SEQ ID NO: 19)

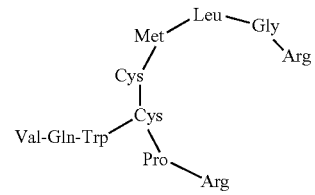

(xvii) Disulfide bond between CysMetLeuGlyArgVal (SEQ ID NO: 32) and ProCysTrpGlnVal (SEQ ID NO: 20):

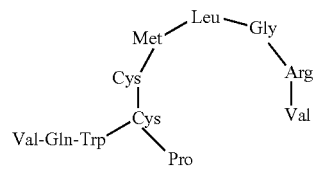

(xviii) Disulfide bond between CysMetLeuGlyArg (SEQ ID NO: 31) and ValTyrArgProCysTrpGlnVal (SEQ ID NO: 21)

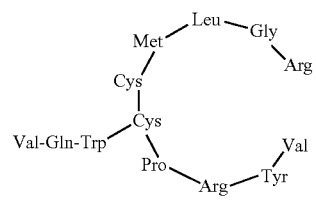

(xix)

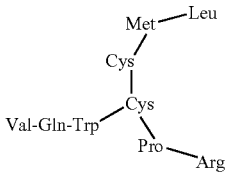 (SEQ ID NO: 22)

(xx)

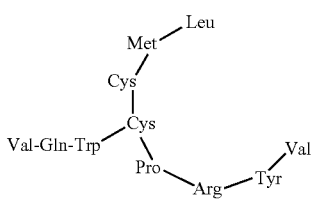

(SEQ ID NO: 23)

(xxi) Disulfide bond between Arg Cys Met Leu (SEQ ID NO: 8) and ArgProCysTrpGlnVal (SEQ ID NO: 24):

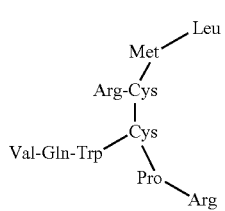

(SEQ ID NO: 24)

(xxii)) Disulfide bond between Arg Cys Met Leu Gly (SEQ ID NO: 33) and ValTyrArgProCysTrpGlnVal (SEQ ID NO: 25)

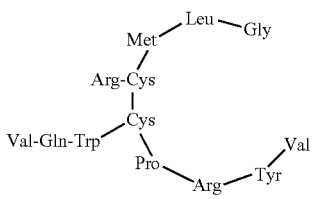

(xxiii) Val Tyr Arg Pro Cys Trp Gln Val (SEQ ID NO: 26)

(xxiv) Arg Pro Cys Trp Gln Val (SEQ ID NO: 27)

(xxv) Cys Trp Gln Val (SEQ ID NO: 28)

(E) a peptide comprising an amino acid Arg Cys Met Leu Gly Arg Val Tyr Arg Pro Cys Trp Gln Val (SEQ ID NO: 29) and salts thereof.

Use of a peptide compound as an active ingredient according to the present invention in production of a food intake regulator, wherein the peptide compound is at least one component selected from the group consisting of (A) to (E) as noted above.

Use of a peptide compound as an active ingredient according to the present invention for food intake suppression of a subject in production of foods, pharmaceuticals, cosmetics and quasi drugs, wherein the peptide compound is at least one component selected from the group consisting of (A) to (E) as noted above.

The present invention also relates to a method of suppressing food intake of a subject by administering an active ingredient to the subject, wherein the active ingredient is at least one component selected from the group consisting of (A) to (E) as described above.

A process for producing a peptide consisting of any one of the above amino acid sequences (i) to (xxv) or a salt thereof according to the present invention, comprising isolating the peptide consisting of any one of the amino acid sequences (i) to (xxv) or a salt thereof from the digests obtained by the enzymatic decomposition of the fish or mammalian melanin-concentrating hormone which is a peptide represented by the above formula (1) or (2) or a salt thereof.

The present invention also relates to a peptide consisting of any one of the above amino acid sequences (i) to (xxv) or a salt thereof.

The peptides having the amino acid sequence (i) to (xxv), respectively, are enzymatic digests of a fish or mammalian melanin-concentrating hormone or a salt thereof which is the peptide represented by the above formula (1) or (2).

Therefore, a food intake regulator can be obtained by using one or more compounds selected from the group consisting of peptides (SEQ ID NOs. 1 to 33) and salts thereof. The present invention further includes the use of at least one compound selected from the group consisting of peptides (SEQ ID NOs. 1 to 33) for production of food intake regulators, foods, pharmaceuticals and quasi drugs. The present invention further includes a method of treating and/or preventing a disease such as obesity by administrating at least one compound selected from the group consisting of peptides (SEQ ID NOs. 1 to 33) to a subject necessary to be treated.

The food intake regulator preferably contains an effective amount of the active ingredient to suppress appetite and food intake in mammals. In addition, the food intake regulator can further contain a pharmaceutically acceptable carriers or a dilution. Moreover, the food intake regulators can be provided in the forms as foods, pharmaceuticals and quasi drugs.

According to the present invention, a food intake regulator can be supplied, which can be administered by a suitable manner such as intravenous injection or can be easily taken through regular diet.

BRIEF DESCRIPTION OF THE DRAWING

FIG. 1 is a graph showing the food intakes.

DETAILED DESCRIPTION OF THE PREFERRED EMBODIMENTS

The food intake regulator according to the present invention comprises a fish or mammalian melanin-concentrating hormone (MCH) or a related substance thereof as an active ingredient. As mentioned above, MCH is known to stimulate food intake when the hormone is injected intracerebroventricularly to rats. Contrary to this food intake stimulation, when the peptide is administered orally, intravenously, intraperitoneally, subcutaneously, or by other modes of administration other than intracerebroventricular administration, the peptide exhibits the effect of food regulation and, thus, is expected to exhibit anti-obesity effect according to the present invention.

Enzymatic digests of MCH also exhibit the same effect. As a result, MCH is considered to express its activity as the food intake regulator through decomposition by the action of biological enzymes (such as peptidase) and endogenous substances in a person or an animal. Therefore, the appetite of the target people or the target animals can be suppressed by allowing them to take the food intake regulator according to the invention.

An embodiment of the food intake regulator according to the present invention uses the common structure between fish and human MCHs. However, it is noted that the peptide having the shorter sequence Gly Arg Val Tyr Arg Pro Cys Trp Gln Val (SEQ ID NO: 34) exhibits no food intake regulation activity.

The food intake regulator according to the present invention has anti-obesity effect. Therefore, the food intake regulator according to the present invention is effective in patients undergoing obesity treatment or in preventing obesity in potentially obese people. Furthermore, the food intake regulator according to the invention is useful in treating various diseases or symptoms of the diseases, which can be improved by appetite regulation.

The present invention includes the use of one or more of the peptides and salts thereof as an active ingredient in products such as food intake regulators, foods and pharmaceuticals. The present invention also includes the use of one or more of the peptides and salts thereof as an active ingredient(s) in production of food intake regulators, foods, and pharmaceuticals. The present invention also includes a process for producing the peptides and salts thereof.

Next, the present invention is described in detail below. The food intake regulator according to the invention contains at least one of the peptides and salts thereof described above as the first to fifth embodiments.

These peptides can also be obtained by peptide synthesis using a general organic chemical liquid-phase or solid-phase method by introducing amino acids stepwise; genetic engineering; or other techniques. Thus, the peptides can also easily be produced according to general chemical synthesis techniques.

Publicly-known methods may be used for synthesis using a liquid-phase or solid-phase synthesis method. A solid-phase synthesis method is preferred using t-butyloxycarbonyl (Boc) or (9-fluorenylmethoxycarbonyl (Fmoc) as a protective group for amino groups. The peptide chains of the peptides as the active ingredient in the food intake regulator according to the present invention can be synthesized by a solid-phase synthesis method using a commercially available peptide synthesizer (available from Applied Biosystems Inc., for example). In addition, the cyclic peptides having the disulfide bonds can be prepared by synthesizing linear peptides according to the above method and air oxidizing them in a diluted solution.

Furthermore, the food intake regulator peptides according to the present invention may be prepared by biosynthesis based on a genetic engineering technique. This technique is preferable when the food intake regulator peptides of relatively long chains are produced. More specifically, a DNA of the nucleotide sequence (including the ATG initiation codon) coding for the amino acid sequence of the desired food intake regulator peptide is synthesized. Then, a recombinant vector is constructed based on the host cells, which has a gene structure for expression. The gene structure may contains the DNA and various regulatory factors to express the peptide of the desired amino acid sequence in host cells (including a promoter, a ribosome binding site, a terminator, an enhancer, and various cis elements regulating the level of expression). A general technique is used to introduce this recombinant vector into the prescribed host cells (e.g., yeast, insect cells, plant cells, and animal cells including mammalian cells) and to cultivate the host cells or the tissues or the individuals containing the host cells under the prescribed conditions. Thus, the desired food intake regulator peptides can be expressed and produced in the host cells. Then, the food intake regulator peptides can be obtained by isolating them from the host cells (or the media, when the peptides are secreted) and purifying the peptides.

Each peptide as an active ingredient can be allowed to form a salt with an inorganic acid or an organic acid, or a salt with an inorganic base or an organic base as needed. The acid and base can be selected depending on the intended use of the salt, and in light of use in foods, cosmetics, and pharmaceuticals.

Thus, the pharmaceutically acceptable salts listed below are preferable. Examples of acid addition salts include hydrochloride, nitrate, sulfate, methanesulfonate, and p-toluenesulfonate, further salts with dicarboxylic acids such as oxalic acid, malonic acid, succinic acid, maleic acid, and fumaric acid, and further salts with monocarboxylic acids such as acetic acid, propionic acid, and butyric acid. In addition, examples of the inorganic bases suitable for formation of salts of the peptide compounds obtained in the present invention include hydroxides, carbonates, and bicarbonates of ammonia, sodium, lithium, calcium, magnesium and aluminum. Examples of the organic bases include salts of mono-, di-, and tri-alkylamines such as methylamine, dimethylamine, and triethylamine, mono-, di-, and tri-hydroxyalkylamine salts, guanidine salt, and N-methylglucosamine salt.

The food intake regulator according to the present invention can be provided with one or more of the peptides of the above-described first to fifth embodiments or salts thereof, as they are. If desired, at least one of the peptides of the above-described first to fifth embodiments or salts thereof can be used in a composition with a secondary component(s) such as carriers, diluents and various additives. The secondary components include diluents, excipients, and various additives, which are typically pharmaceutically acceptable depending on the intended use. The secondary components can vary based on the intended uses and the formulation modes of the food intake regulator. The secondary components may also include water, various organic solvents, and various buffers, as well as fillers, expanders, binders, humectants, surfactants, pigments, and fragrances.

The food intake regulator according to the present invention can be provided as pharmaceutical compositions, foods such as solid food, semi-solid food, and liquid food including beverages and in various other forms. For example, the food intake regulator according to the invention can be provided in various forms such as liquid, emulsion, dispersion, powder, granule, tablet, capsule, paste, and cream.

A agent for treating and/or preventing obesity as one embodiment of the present invention can be produced with one or more of the peptides and salts thereof as an active ingredient. In this case, the food intake regulator can be formulated into preparations in forms such as injection, oral solution, tablet, granule, powder, capsule, suppository, ointment, nasal drop, eye drop, and patch, by appropriately mixing the active ingredient with an additive such as an excipient for preparing the food intake regulator, as needed.

Examples of the additives used in the above preparations include magnesium stearate, talc, lactose, dextrin, starches, methyl cellulose, fatty acid glycerides, water, propylene glycol, macrogols, alcohol, crystalline cellulose, hydroxypropyl cellulose, low substituted hydroxypropyl cellulose, carmelloses, povidone, polyvinyl alcohol, and calcium stearate. These additives can be used alone or in combination of two or more of them. In these cases, one or more components selected from colorants, stabilizers, antioxidants, preservatives, pH regulators, tonicity agents, solubilizers and soothing agents can be added as needed. Granules, tablets, and capsules can also be coated with a coating base such as hydroxypropylmethyl cellulose or hydroxypropylmethyl cellulose phthalate. These preparations can contain one or more of the peptides and salts thereof as an active ingredient or ingredients, at a percentage of 0.01 wt % or more, preferably 0.01 to 70 wt %.

Examples of the pharmaceutical forms especially preferable to infusion (injection) administration include sterile aqueous solutions (water-soluble) or dispersions and sterile powders for the instant production of sterile injections or dispersions. In either case, these formations must be sterile and fluids which can disperse broadly enough to easily come into an injectable state. These formations must be stable and protected against contamination by microorganisms such as bacteria and fungi during their production and storage. The carriers may be solvents or liquid media for dispersion, and examples of the carriers include water, ethanol, polyol (e.g., glycerol, polyethylene glycol, and liquid polyethylene glycol), preferable mixtures thereof, and vegetable oils. Appropriate fluidity of the solution can be maintained, for example by using a coating agent such as lecithin, maintaining the desired particle size for dispersions, or using a surfactant. Microbial activity can be prevented, for example by adding at least one of various antibacterial agents and antifungal agents such as paraben, chlorobutanol, phenol, sorbic acid, and thimerosal. In many cases, one or more isotonic agents such as sugar and sodium chloride are preferably contained. The absorption of the infusion (injection) composition can be prolonged by using an absorption-delaying agent(s) such as aluminum monostearate and gelatin in the composition.

The sterile infusion or injection solution is produced by mixing a necessary amount of at least one of the active compounds into an appropriate solvent, which may contain at least one of various other components listed above as desired and then filtering and sterilizing the solution. Generally, an agent in which the component(s) are dispersed, can be produced by incorporating at least one of various sterile active ingredients into a sterile carrier, which may contain the base medium for dispersion and at least one of the other necessary components listed above. For the sterile powder for the preparation of the sterile infusion solution, a preferable process for producing the powder is that using a freeze-drying technique combined with vacuum drying, after the addition of any additional necessary ingredient(s) mentioned above concerning the infusion or injection administration.

When the preparations are prepared, menthol, citric acid and salts thereof, and flavoring agents such as fragrances can be added as needed. In addition, the food intake regulator obtained according to the present invention can also be used with the other ingredient(s) that are useful for the desired treatment.

The food intake regulators according to the present invention are not directly administered intracerebroventricularly to mammals including humans but orally or parenterally (e.g., percutaneously, intravenously, or intraperitoneally). The dosage varies depending on the animal species, the race, sex, symptoms, body weight, age, and blood pressure of the patient or the potential patient to be treated, the mode of administration. Therefore, there is no fixed general dosage regimen. When the food intake regulator is orally administered to an adult human, its dosage is usually 0.1 to 2000 mg/kg of body weight/day, preferably 1 to 500 mg/kg of body weight/day and usually administered once a day, or in 2 or 3 times as divided daily doses. However, the dosage can be appropriately selected depending on the degree of the symptoms.

The MCH obtained in the present invention or enzymatic digests thereof exhibit an excellent food intake regulation effect. Since these substances have no specifically offensive smell, taste, or color, they are easily taken orally. For these reasons, one or more of the peptides and salts thereof as an active ingredient can also be preferably added to products other than pharmaceuticals. For example, these ingredients can be supplied by adding them to solid foods, semi-solid foods, and liquid foods such as jellies, candies, granule confectionery, tablet confectionery, beverages, yogurts, soups, noodles, rice crackers, Japanese-style confectionery, Western-style confectionery, frozen desserts, baked pastry, and seasonings, respectively. In addition, as non-food products other than pharmaceuticals, these ingredients can also be provided in forms such as cosmetics or sanitary goods, and luxury goods. Examples of quasi drugs, one of these non-food products, include hair restorers and tonics, depilatories, hair dyes, decolorizers, permanent wave agents, bath agents, medicated cosmetics and medicated soaps, medicated toothpastes, refrigerants, underarm deodorants, and talcum powders.

The content of at least one of MCH, the enzymatic digests thereof and salts thereof in these non-pharmaceutical products may be selected depending on the intended use and function of the products. It can be selected for example from the range of 0.01 wt % or more, preferably 0.1 to 70 wt %. Regarding cosmetics, various forms of cosmetics such as lotions, creams, powders, and emulsion gels can be prepared by using various solid, semi-solid, or liquid cosmetic bases, and the food intake regulator or the food intake regulator composition in addition to the other active ingredient(s) used to obtain the target cosmetic effect.

Examples of the protease which can be used for the preparation of enzymatic digests of mammalian MCH include trypsin. For enzymatic decomposition, an enzyme alone may be used or in combination of two or more enzymes. In addition, such proteases are divided into endopeptidases which specifically recognize and cleave internal sequences of a protein and exopeptidases which cleave one or two amino acid residues at a time from the termini of a protein. Therefore, various peptide chains can be produced by combining the endopeptidase and the exopeptidase as needed. For enzymatic hydrolysis, 0.001 to 10 wt % of an enzyme(s) is added to the substrate, and the pH of the solution is set to the optimum pH of the enzyme used.

The peptide(s) according to the present invention can be added in any step for production of the food intake regulators, pharmaceuticals and quasi drugs.

EXAMPLES

Next, the embodiments for carrying out the present invention are described in detail below by using Examples, but the invention is not limited to the Examples below.

Example 1

Synthesis of a Peptide Consisting of the Amino Acid Sequence of SEQ ID NO: 3

A human MCH in a chain form was synthesized with a peptide synthesizer (Model 433A, Applied Biosystems) by FastMoc chemistry on a 0.25-mmol scale. As a preloaded resin, 490.0 mg of Fmoc-Val-HMP resin (0.51 mmol/g) was used. 8 mL of cleavage cocktail B (a mixed solution of 0.75 g of phenol, 0.25 mL of 2,3-ethanedithiol, 0.5 mL of thioanisole, 0.5 mL of distilled water, and 10 mL of trifluoroacetic acid) was added to 31.6 mg of the resin containing the synthetic human MCH in a chain form thus obtained, which was then stirred at 0° C. for 15 minutes. The resin was brought back to room temperature, stirred for 1.5 hours, and filtered (Assist cc.07). The filtrate was dropped into two centrifugation tubes each containing 7.5 mL of ice-cold t-butyl methyl ether. After the tubes were stirred, they were centrifuged (4° C., 3000 rpm, 10 minutes). The supernatant was decanted and then 7.5 mL of ice-cold t-butyl methyl ether was added to the precipitate and the same procedure was repeated to obtain a chained MCH crude peptide preparation. The crude peptide preparation thus obtained was first dissolved in a 0.1% acetic acid aqueous solution and then freeze-dried to obtain its acetate.

Example 2

Synthesis of Mammalian MCH

A human MCH in a chain form was synthesized with a peptide synthesizer (Model 433A, Applied Biosystems) by FastMoc chemistry on a 0.25-mmol scale. As a preloaded resin, 490.0 mg of Fmoc-Val-HMP resin (0.51 mmol/g) was used. 1 mL of cleavage cocktail B (a mixed solution of 0.75 g of phenol, 0.25 mL of 2,3-ethanedithiol, 0.5 mL of thioanisole, 0.5 mL of distilled water, and 10 mL of trifluoroacetic acid) was added to 48.9 mg of the resin including the synthetic human chained MCH thus obtained, which was then stirred at 0° C. for 15 minutes. The resin was brought back to room temperature, stirred for 1.5 hours, and filtered (Assist cc.07). The filtrate was dropped into two centrifugation tubes each containing 7.5 mL of ice-cold t-butyl methyl ether. After the tubes were stirred, they were centrifuged (4° C., 3000 rpm, 10 minutes). The supernatant was decanted and then 7.5 mL of ice-cold t-butyl methyl ether was added to the precipitate and a similar operation was conducted to obtain a chained MCH crude peptide preparation. After that, the crude peptide preparation thus obtained was first dissolved in a 0.1% trifluoroacetic acid aqueous solution and then freeze-dried to obtain 18.9 mg of the desired peptide. The intermolecular disulfide bonds were formed by dissolving 18.9 mg of this peptide in 500 mL of 20 mM ammonium carbonate and stirring the mixture at room temperature for 6 days. Then, the mixture was freeze-dried to obtain the peptide as the final peptide.

Example 3

Preparation of Tryptic Digests of Mammalian MCH

After a phosphate buffer (pH 8, 200 µL) was added to mammalian MCH (1.08 mg) and dissolved, trypsin (1 U/0.25 mg) was added to the mixture, which was then allowed to react at 25° C. for 4 hours. After that, the reaction was stopped at 95° C. for 10 minutes, and the mixture was freeze-dried to obtain the desired product, quantitatively.

Example 4

Synthesis of a Peptide Consisting of the Amino Acid Sequence of SEQ ID NO: 29

The peptide consisting of the amino acid sequence of SEQ ID NO: 29 was synthesized with a peptide synthesizer (Model 433A, Applied Biosystems) by FastMoc chemistry on a 0.25-mmol scale. As a preloaded resin, 490.0 mg of Fmoc-Val-HMP resin (0.51 mmol/g) was used. 4 mL of cleavage cocktail B (a mixed solution of 0.75 g of phenol, 0.25 mL of 2,3-ethanedithiol, 0.5 mL of thioanisole, 0.5 mL of distilled water, and 10 mL of trifluoroacetic acid) was added to 100 mg of the resin including the desired peptide thus obtained, which was then stirred at 0° C. for 15 minutes. The resin was brought back to room temperature, stirred for 1.5 hours, and filtered (Assist cc.07). The filtrate was dropped into two centrifugation tubes each containing 7.5 mL of ice-cold t-butyl methyl ether. After the tubes were stirred, they were centrifuged (4° C., 3000 rpm, 10 minutes). The supernatant was decanted and then 7.5 mL of ice-cold t-butyl methyl ether was added to the precipitate and a similar operation was conducted to obtain the peptide. The crude peptide obtained was first dissolved in a 0.1% acetic acid aqueous solution and then freeze-dried to obtain its acetate.

Test Example

Measurement of Food Intake

Male SD rats (Sprague-Dawley, body weight of 275±25 g) were housed and fed in 45×23×15-cm APECR cages, five rats per cage. The rats were acclimated for 1 week or more on a 12-h light/12-h dark cycle at a room temperature of 22 to 24° C. and a humidity of 60 to 80% with free access to food and water before the test. The rats used for the test were fasted for 12 hours overnight before initiation of the test. After fasting, the samples to be tested as the food intake regulator were dissolved in saline and the dissolved test samples were intravenously given (150 µg/body) to the rats, respectively, in the treatment group and, then, their food intakes were measured 1, 2, 4, and 6 after administration. In contrast, in the control group, saline was intravenously given and their food intakes were measured in the same way.

(Test Samples)
(1) Fish melanin-concentrating hormone (MCH) which is the peptide having the formula (1)
(2) Mammalian melanin-concentrating hormone (MCH) which is the peptide having the formula (2)
(3) Peptide consisting of the amino acid sequence Asp Phe Asp Met Leu Arg Cys Met Leu Gly Arg Val Tyr Arg Pro Cys (SEQ ID NO: 3)
(4) Tryptic digests of mammalian melanin-concentrating hormone (MCH). They contain all of peptides (i) to (xxv).
(5) Peptide consisting of the amino acid sequence Arg Cys Met Leu Gly Arg Val Tyr Arg Pro Cys Trp Gln Val (SEQ ID NO: 29)
(Test Results)
As shown in FIG. 1, it was confirmed that the MCH or enzymatic digests thereof according to the present invention act to significantly inhibit or suppress food intake.

As mentioned above, the effect of the food intake regulator was noted by allowing the rats to take the MCH or the enzymatic digests thereof. This shows that the MCH and related substances thereof are useful in improving and treating as well as preventing obesity, and that they can be used as pharmaceuticals, quasi drugs, health foods, functional foods, and other products having the above bioactivity.

What is claimed is:

1. A method for treating or preventing obesity, comprising administering an active ingredient to a subject in an amount effective to suppress food intake thereby treating or preventing obesity, wherein the active ingredient is a peptide consisting of the amino acid sequence Arg Cys Met Leu Gly Arg Val Tyr Arg Pro Cys Trp Gln Val (SEQ ID NO: 29), or salts thereof.

2. A method according to claim 1, wherein the active ingredient further comprises at least one component selected from the group consisting of:

(A) a fish melanin-concentrating hormone which is a peptide represented by the following formula (1):

(1)

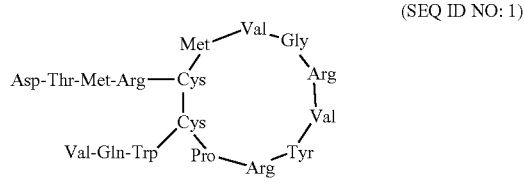

(SEQ ID NO: 1)

and salts thereof;

(B) a mammalian melanin-concentrating hormone which is a peptide represented by the following formula (2):

(2)

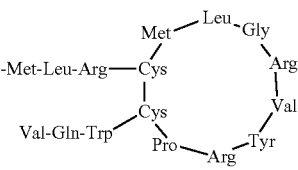

(SEQ ID NO: 2)

and salts thereof;

(C) a peptide consisting of an amino acid sequence represented by Asp Phe Asp Met Leu Arg Cys Met Leu Gly Arg Val Tyr Arg Pro Cys Trp Gln Val (SEQ ID NO: 3) and salts thereof;

(D) a peptide represented by one of the following amino acid sequences represented by any one of the following (i) to (xxv) and salts thereof:
  (i) Asp Phe Asp Met Leu Arg (SEQ ID NO: 4)
  (ii) Asp Phe Asp Met Leu (SEQ ID NO: 5)
  (iii) Asp Met Leu Arg (SEQ ID NO: 6)
  (iv) Arg Cys Met Leu (SEQ ID NO: 7)

(v) peptide with disulfide bond between Arg Cys Met Leu (SEQ ID NO: 8) and ArgProCysTrp (SEQ ID NO: 30):

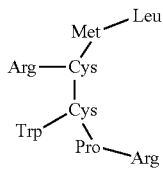

(vi)

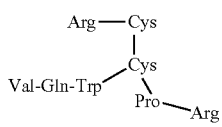
(SEQ ID NO: 9)

disulfide bonded to ArgCys
(vii) Met Leu Gly (SEQ ID NO: 10)
(viii) Leu Gly Arg (SEQ ID NO: 11)
(ix) Gly Arg Val Tyr (SEQ ID NO: 12)
(x) Leu Gly Arg Val Tyr (SEQ ID NO: 13)
(xi) Val Tyr (SEQ ID NO: 14)
(xii)

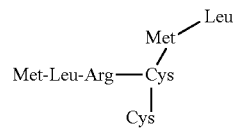
(SEQ ID NO: 15)

disulfide bonded to Cys
(xiii)

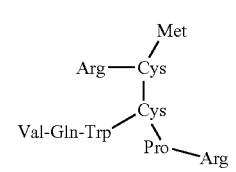
(SEQ ID NO: 16)

disulfide bonded to ArgCysMet
(xiv)

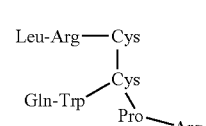
(SEQ ID NO: 17)

disulfide bonded to LeuArgCys (xv)

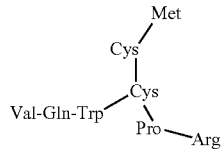
(SEQ ID NO: 18)

disulfide bonded to CysMet (xvi) peptide with ArgProCysTrpGlnVal (SEQ ID NO: 19) disulfide bonded to CysMetLeuGlyArg (SEQ ID NO: 31):

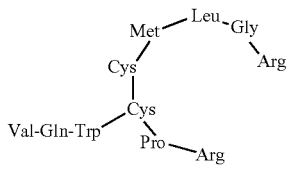

(xvii) peptide with CysMetLeuGlyArgVal (SEQ ID NO: 32) disulfide bonded to ProCysTrpGlnVal (SEQ ID NO: 20):

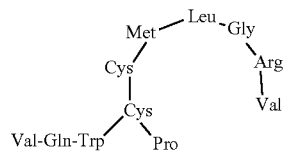

(xviii) peptide with CysMetLeuGlyArg (SEQ ID NO: 31) disulfide bonded to ValTyrArgProCysTrpGlnVal (SEQ ID NO: 21):

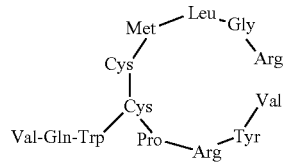

(xix)

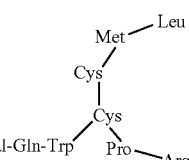
(SEQ ID NO: 22)

disulfide bonded to CysMetLeu (xx)

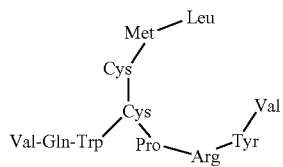
(SEQ ID NO: 23)

disulfide bonded to CysMetLeu (xxi) peptide with Arg Cys Met Leu (SEQ ID NO: 8) disulfide bonded to ArgProCysTrpGlnVal (SEQ ID NO: 24):

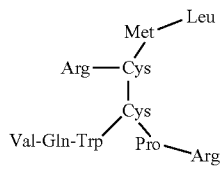

(xxii) peptide with Arg Cys Met Leu Gly (SEQ ID NO: 33) disulfide bonded to ValTyrArgProCysTrpGlnVal (SEQ ID NO: 25):

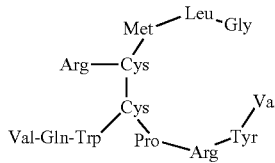

(xxiii) Val Tyr Arg Pro Cys Trp Gln Val (SEQ ID NO: 26)
(xxiv) Arg Pro Cys Trp Gln Val (SEQ ID NO: 27) and
(xxv) Cys Trp Gln Val (SEQ ID NO: 28).

3. A method of suppressing food intake of a subject, comprising
administering an active ingredient to the subject in an amount necessary for the food intake suppression,
wherein the active ingredient is a peptide consisting of the amino acid sequence Arg Cys Met Leu Gly Arg Val Tyr Arg Pro Cys Trp Gln Val (SEQ ID NO: 29), or salts thereof.

4. A method according to claim 3,
wherein the active ingredient further comprises at least one component selected from the group consisting of:
(A) a fish melanin-concentrating hormone which is a peptide represented by the following formula (1):

(1)

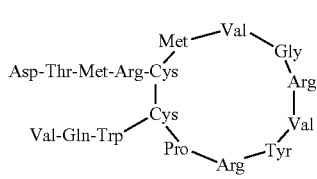
(SEQ ID NO: 1)

and salts thereof;

(B) a mammalian melanin-concentrating hormone which is a peptide represented by the following formula (2):

(2)

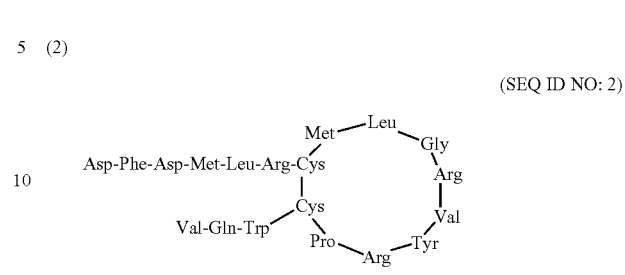
(SEQ ID NO: 2)

and salts thereof;

(C) a peptide consisting of an amino acid sequence represented by Asp Phe Asp Met Leu Arg Cys Met Leu Gly Arg Val Tyr Arg Pro Cys Trp Gln Val (SEQ ID NO: 3) and salts thereof;

(D) a peptide represented by one of the following amino acid sequences represented by any one of the following (i) to (xxv) and salts thereof:

(i) Asp Phe Asp Met Leu Arg (SEQ ID NO: 4)
(ii) Asp Phe Asp Met Leu (SEQ ID NO: 5)
(iii) Asp Met Leu Arg (SEQ ID NO: 6)
(iv) Arg Cys Met Leu (SEQ ID NO: 7)
(v) peptide with disulfide bond between Arg Cys Met Leu (SEQ ID NO: 8) and ArgProCysTrp (SEQ ID NO: 30):

(vi)

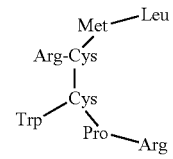
(SEQ ID NO: 9)

disulfide bonded to ArgCys (vii) Met Leu Gly (SEQ ID NO: 10)
(viii) Leu Gly Arg (SEQ ID NO: 11)
(ix) Gly Arg Val Tyr (SEQ ID NO: 12)
(x) Leu Gly Arg Val Tyr (SEQ ID NO: 13)
(xi) Val Tyr (SEQ ID NO: 14)
(xii)

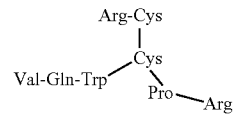
(SEQ ID NO: 15)

disulfide bonded to Cys (xiii)

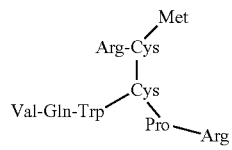
(SEQ ID NO: 16)

disulfide bonded to ArgCysMet (xiv)

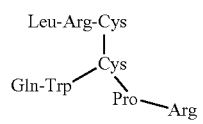
(SEQ ID NO: 17)

disulfide bonded to LeuArgCys (xv)

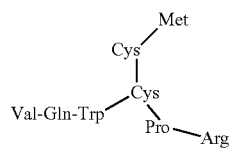
(SEQ ID NO: 18)

disulfide bonded to CysMet (xvi) peptide with ArgProCysTrpGlnVal (SEQ ID NO: 19) disulfide bonded to CysMetLeuGlyArg (SEQ ID NO: 31):

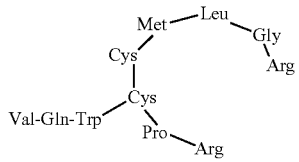

(xvii) peptide with CysMetLeuGlyArgVal (SEQ ID NO: 32) disulfide bonded to ProCysTrpGlnVal (SEQ ID NO: 20):

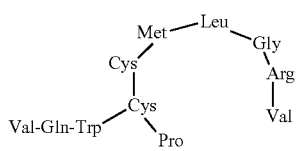

(xviii) peptide with CysMetLeuGlyArg (SEQ ID NO: 31) disulfide bonded to ValTyrArgProCysTrpGlnVal (SEQ ID NO: 21):

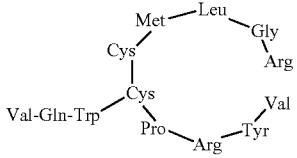

(xix)

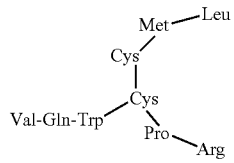
(SEQ ID NO: 22)

disulfide bonded to CysMetLeu (xx)

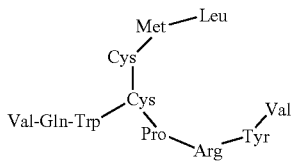
(SEQ ID NO: 23)

disulfide bonded to CysMetLeu (xxi) peptide with Arg Cys Met Leu (SEQ ID NO: 8) disulfide bonded to ArgProCysTrpGlnVal (SEQ ID NO: 24):

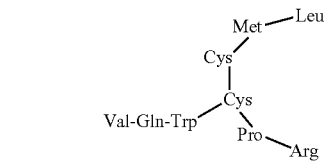

(xxii) peptide with Arg Cys Met Leu Gly (SEQ ID NO: 33) disulfide bonded to ValTyrArgProCysTrpGlnVal (SEQ ID NO: 25):

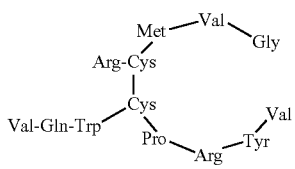

(xxiii) Val Tyr Arg Pro Cys Trp Gln Val (SEQ ID NO: 26)
(xxiv) Arg Pro Cys Trp Gln Val (SEQ ID NO: 27) and
(xxv) Cys Trp Gln Val (SEQ ID NO: 28).

5. A method according to claim 4, wherein the active ingredient is administered in a form of a composition comprising the active ingredient and a carrier or a diluent.

6. A method according to claim 4, wherein the composition is formulated in a form of a pharmaceutical, a cosmetic or a quasi drug.

7. A method according to claim 4, wherein the active ingredient is contained in a food and the food is administered.

* * * * *